(12) United States Patent
Pier et al.

(10) Patent No.: US 6,722,062 B2
(45) Date of Patent: Apr. 20, 2004

(54) CAPSULAR POLYSACCHARIDES FROM ENTEROCOCCI

(75) Inventors: Gerald B. Pier, Brookline, MA (US); Johannes Huebner, Brookline, MA (US); Ying Wang, Brookline, MA (US); Lawrence Madoff, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 10/094,134

(22) Filed: Mar. 11, 2002

(65) Prior Publication Data

US 2002/0122809 A1 Sep. 5, 2002

Related U.S. Application Data

(60) Continuation-in-part of application No. 09/436,238, filed on Nov. 9, 1999, now abandoned, which is a division of application No. 09/134,923, filed on Aug. 17, 1998, now Pat. No. 5,989,542.

(60) Provisional application No. 60/056,096, filed on Aug. 20, 1997.

(51) Int. Cl.[7] .................. A01N 63/00; A61K 39/02; C12N 9/64; C12N 1/12; C12N 1/20

(52) U.S. Cl. .................. 36/547; 424/93.48; 424/130.1; 424/150.1; 424/184.1; 424/234.1; 424/278.1; 435/226; 435/252.1; 435/252.33; 435/257; 435/259; 436/512; 436/547; 436/548; 514/53; 514/54; 514/127; 530/387.1

(58) Field of Search ................. 424/93.4, 130, 424/234.1, 130.1, 150.1, 184.1, 278.1; 435/226, 252.1, 252.33, 257, 259; 514/53, 54, 127; 436/512, 547, 548; 530/387.1

(56) References Cited

U.S. PATENT DOCUMENTS

| | | | |
|---|---|---|---|
| 4,242,501 A | 12/1980 | Cano et al. | 535/1 |
| 4,857,512 A | 8/1989 | Wagner et al. | 514/54 |
| 4,900,677 A | 2/1990 | Hewitt | 439/259 |
| 5,292,652 A | 3/1994 | Dovey et al. | 435/226 |
| 5,472,872 A | 12/1995 | Mead et al. | 435/252.33 |
| 5,681,736 A | 10/1997 | Pace et al. | 435/252.1 |

OTHER PUBLICATIONS

Wicken, et al., "Structure of Intracellular Teichoic Acids from Group D. *Streptococci*," *Biochem J.* 87:54–62 (1963).

*Primary Examiner*—Lynetter R. F. Smith
*Assistant Examiner*—Jana Hines
(74) *Attorney, Agent, or Firm*—Michael A. Sanzo; Fitch, Even, Tabin & Flannery

(57) ABSTRACT

The present invention is directed to a method for purifying polysaccharides capable of inducing the production of high titers of opsonic antibodies that kill strains of enterococcal bacteria. In addition, the invention is directed to the antigens produced by this purification method and to vaccines which utilize such antigens.

7 Claims, 1 Drawing Sheet

CAPSULAR POLYSACCHARIDES FROM ENTEROCOCCI

CROSS REFERENCE TO RELATED APPLICATIONS

The present application is a continuation-in-part of U.S. Ser. No. 09/436,238, filed on Nov. 9, 1999 (now abandoned). The '238 application is a division of U.S. Ser. No. 09/134, 923, filed Aug. 17, 1998 (now U.S. Pat. No. 5,989,542). The '238 application claims priority to U.S. provisional application No. 60/056,096, filed on Aug. 20, 1997.

FIELD OF THE INVENTION

The present invention is directed to polysaccharides that can be used to induce the production of antibodies to specific strains of enterococcal bacteria. The polysaccharides may be incorporated into a vaccine or used in vitro to assay for the presence of bacteria in a sample of biological fluid.

BACKGROUND OF THE INVENTION

Enterococci are frequently causes of serious infections in newborns and severely immunocompromised patients. Until recently, infections have been adequately controlled using antibiotics. However, drug-resistant bacterial strains are emerging, and infection by strains resistant to all presently available antibiotics may become a serious problem in the near future. It is therefore essential that new methods for controlling enterococcal infections be developed.

The present invention describes a procedure for purifying polysaccharides from the cell membranes of *E. faecalis*. When administered to an appropriate host, these antigens induce the production of high titers of opsonic antibodies that kill both *E. faecalis* and *E. faecium*.

SUMMARY OF THE INVENTION

The present invention is based upon the discovery that a polysaccharide antigen can be isolated from *E. faecalis* bacteria and that this antigen can be used to produce antibodies that kill two different species of enterococci, *E. faecalis* and *E. faecium*.

*E. faecalis* bacteria, preferably bacteria deposited as ATCC number 202159, are sequentially digested with mutanolysin/lysozyme, nucleases (both RNase and DNase) and pronase. The digestion product is then size fractionated and high molecular weight fractions containing the immunogenic polysaccharide are selected. The preferred method for carrying out the size fractionation step is to use a column of Sephacryl S-500™ (Pharmacia, cross-linked allyl dextran/N,N'-methylenebiscraylamide) and to collect fractions corresponding to the void volume.

Structural characterization of the high molecular weight polysaccharide thus obtained has demonstrated that it has a disaccharide, α-D-GlcP-(1→2)-α-D-GlcP, linked to a glycerol teichoic acid backbone via the number 2 carbon of glycerol. There are phosphodiester bonds between the first carbon of the glycerol backbone and the sixth carbon of the glucose disaccharide. Substantially purified high molecular weight polysaccharides having these characteristics are part of the invention. As used herein, the term "substantially purified" refers to polysaccharides that are essentially free from other biological materials. Typically the polysaccharides in such a preparation will constitute at least 80% of the total biological material present with higher percentages being preferred.

Once obtained, the high molecular weight polysaccharides may be incorporated as part of a pharmaceutically acceptable preparation and administered to an animal, e.g., a mouse, rabbit, sheep, goat etc., in order to generate antibodies that react with *E. faecalis*. Alternatively the high molecular weight polysaccharide can be incorporated into a vaccine and administered to people in order to evoke an immune response. As used herein, the term "immune response" means that the administration of vaccine confers upon the recipient protective immunity to subsequent challenge by *E. faecalis* bacteria.

Lower molecular weight polysaccharides may also be generated from the preparations described above. In order to destroy phosphodiester-linked materials, e.g., teichoic acid, the size fractionated material may be treated with hydrogen fluoride. The substantially purified low molecular weight polysaccharides thus obtained may be coupled to a protein or other suitable carrier and then used to generate antibodies or as vaccines in the same manner discussed above.

The high or low molecular weight polysaccharide-containing vaccines may be administered to patients at high risk for enterococci infection. Alternatively, they may be administered to a healthy individual for the purpose of developing antibodies that can be administered to an infected patient. Antibodies developed in a human or other species may also be used in assays to determine whether *E. faecalis* is present in a biological fluid. The present invention includes both the vaccines for immunizing patients as well as the immunization procedure itself.

DETAILED DESCRIPTION OF THE INVENTION

Figure 1:
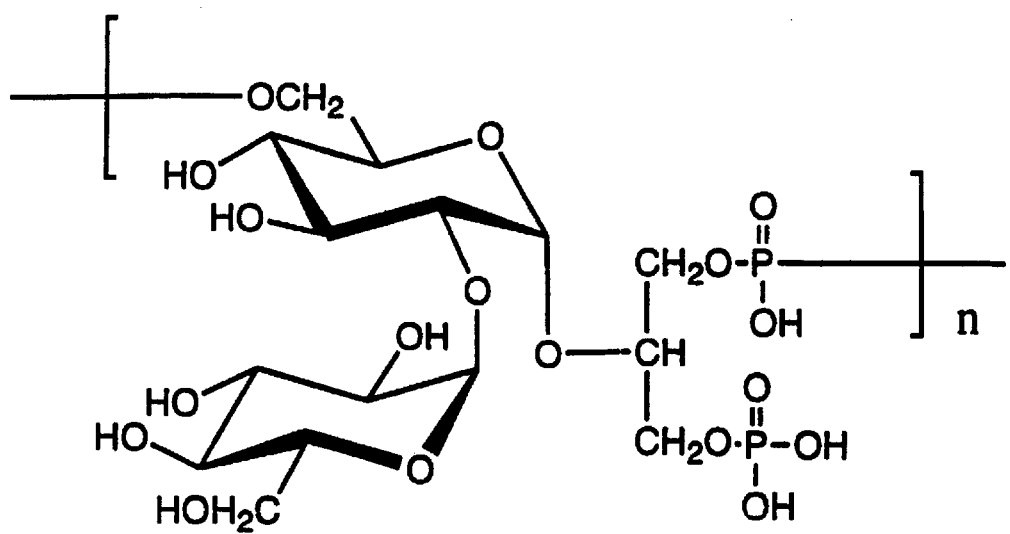
FIG. 1: This shows a polysaccharide that was isolated from *E. faecalis*. The structure consists of two molecules of glucose and one molecule of glycerol di-phosphate linked together as shown. The "n" is the number of repeating units and is in the range of 2–5000.

The present invention is directed to a method for purifying a polysaccharide from enterococcal bacteria and to the use of this polysaccharide for the production of high titers of opsonic killing antibodies. Bacteria having appropriate polysaccharides are first selected and then used as a source of antigen in carrying out the purification. Using a strain of *E. faecalis*, a unique polysaccharide has been isolated that contains a trisaccharide component in a repeating unit with a structure of 6-α-D-GlcP-α-1→2[(2→1)-α-D-GlcP]-glycerol$(PO_4)_2$-3→(see FIG. 1). This polysaccharide is effective in generating highly specific antibodies to both *E. faecalis* and *E. faecium*.

A. Selection of Bacteria

The preferred source of bacteria for purifying the polysaccharide descried herein is Applicants' ATCC deposit number 202159 (deposited on Jul. 30, 1998 at the American Type Culture Collection, Manassas, Va.). Alternatively, an appropriate enterococcal strain may be selected for purification empirically. To do this, different strains of killed bacteria are injected into a host capable of producing antibodies and the sera of the treated animals are tested for their ability to kill a variety of enterococcal strains. For example, rabbits may be immunized with different strains of gentamicin-killed *E. faecalis* and the rabbit sera tested in an opsonophagocytic assay to quantify killing activity against both the homologous bacterial strain and other strains of enterococci. Sera found to have the ability to kill bacterial strains at high dilutions suggest that the bacteria used in immunizations should be a good choice as a source of antigen for purification.

In cases where bacterial strains are selected empirically, those that have generated a highly potent rabbit serum will be tested to confirm that the antigen responsible is a polysaccharide. This may be accomplished by allowing the rabbit serum to interact with the homologous bacterial strain (i.e., the same strain used to immunize rabbits) and subsequently testing the serum to determine if its killing activity has been maintained. If the activity is being caused by the specific interaction of antibody with cell surface bacterial antigen, this pretreatment should result in a loss of subsequent killing activity. If the antigen targeted by the antibody is a polysaccharide, then the ability of the homologous strain to reduce killing activity should be lost if the strain is treated with sodium periodate prior to incubation with serum but not if the bacteria are treated with pronase E.

B. Purification Procedure

Procedure A: Isolation of High Molecular Weight Polysaccharides

The purification method involves first growing a selected strain of enterococcal bacteria, preferably the aforementioned deposited ATCC strain, in an appropriate growth medium. The bacteria are collected, e.g., by centrifugation, and then digested using, first, a combination of mutanolysin and lysozyme and then nucleases. The latter digestion should be performed using a combination of DNases and RNases and, preferably, should be allowed to go to near completion. Proteins are then degraded using one or more peptidases, e.g. with pronase E. The final digest is centrifuged to remove cellular debris and the polysaccharide is then precipitated, preferably with ethanol. The precipitate is reconstituted in distilled water or other suitable buffer and then size fractionated using column chromatography. Fractions collected from the column may be assayed for high molecular weight polysaccharide antigens. It is preferred that size fractionation take place on a Sephacryl S-500™ (Pharmacia Inc., cross-linked allyl dextran/N, N'methylenebiscray-lamide) column using a buffer such as ammonium carbonate. Under these circumstances, the desired polysaccharides will elute with the void volume of the column. The polysaccharides may then be dialyzed against water and lyophilized.

The polysaccharides obtained as described above have been found to consist of a repeating disaccharide unit with a structure of 6-α-D-GlcP-α-1→2[(2→1)-α-D-GlcP]-glycerol($PO_4$)$_2$-3→. The backbone of the polysaccharide is a disaccharide containing one molecule of glucose linked alpha 1→2 to a molecule of glycerol phosphate, which, in turn, is linked via a phosphodiester bond to the number 6 carbon of the glucose residue in the next repeat unit. A side chain consisting of a single glucose residue linked alpha 1→2 to the glucose residue in the backbone is also present. The high molecular weight polysaccharides may be used directly to generate antibodies against E. faecalis by injecting them either into a human or animal, e.g., mouse, rabbit, goat, sheep etc., or they may be digested into smaller fragments as described below.

Purification B: Isolation of Low Molecular Weight Polysaccharides

Contaminating antigens may be removed by ion exchange chromatography. For example, chromatography may be performed on a Q-column in a buffer at about neutral pH and using a salt gradient, e.g., a gradient of sodium chloride from about 0 to 1.0 M. It has been found that this procedure will produce polysaccharides that are pure and highly antigenic.

C. Chemical Composition of Isolated Polysaccharide

The structure of a polysaccharide isolated from E. faecalis by the methods described above has been investigated using chemical and spectroscopic methods. The polysaccharide contains a repeating disaccharide component with a structure of 6-α-D-GlcP-α-1→2[(2→1)-α-D-GlcP]-glycerol ($PO_4$)$_2$-3→. The polysaccharide may contain as few as 2 repeating units and as many as 5,000. Polysaccharide structure may be determined by NMR including $^1$D, $^1$H and $^{13}$C, 2D TOCSY, DQF-COSY, NOESY and HMQC. The structure of the composition may also be verified by GC/MS analysis of its hydrolyzed alditol acetate derivatives.

D. Use of Purified Polysaccharides in an Enterococcal Vaccine

The present invention is also directed to the polysaccharide antigens produced by the purification method described above and to methods for using such antigens. Preferably, the antigens will be used as part of a vaccine to induce the production of antibodies in healthy individuals. Possible target populations for vaccination include immunocompromised patients that are susceptible to systemic enterococcal infection. Preferred populations include oncology patients, transplant patients, neonates, and premature infants.

Typically, a vaccine will contain between 0.1 and 1000 µg of polysaccharide in a volume of between about 0.5 and 5 ml. Formulation may take place using standard methods such as those described in *Remington's Pharmaceutical Sciences* (Mack Publishing Co., Easton, Pa. 16th ed. (1982)). Vaccines will generally be designed for parenteral administration, although the present invention is compatible with other forms of administration as well. Immunization procedures will typically involve several inoculations with vaccine (e.g., 3 inoculations) separated by intervals of 3 to 10 weeks. Procedures for optimizing inoculation schedules and the other parameters associated with immunization are well known in the art.

Preferably, the polysaccharides used in vaccines will have 200 to 5,000 repeating disaccharide units, i.e., n in FIG. 1 will be 200–5,000. Vaccines in which polysaccharide is conjugated to protein may also be used and, for these, n should preferably be 2–2,000. In a conjugate vaccine, an antigenic molecule, polysaccharide is covalently linked to a "carrier" protein or polypeptide. The linkage serves to increase the antigenicity of the conjugated molecule. Methods for forming conjugate vaccines are well known in the art (Jacob, et al, *Eur. J. Immunol.* 16:1057–1062(1986); Parker, et al., In: *Modern Approaches to Vaccines*, Chanock, et al., eds, pp. 133–138, Cold Spring Harbor Laboratory, Cold Spring Harbor, N.Y. (1983); Zurawski, et al., *J. Immunol.* 121:122–129 (1978); Klipstein, et al., *Infect. Immun.* 37:550–557(1982); Bessler, *Immunobiol.* 170:239–244 (1985); Posnett, et al., *J. Biol. Chem.* 263:1719–1725 (1988); Ghose, et al., Molec. *Immunol.* 25:223–230 (1988); all of which references are incorporated herein by reference).

A prototype model for conjugate vaccines was developed against Hemophilus influenzae (Anderson, *Infec. and Immun.* 39:223–238 (1983); Chu, et al., *Infect. Immmun.* 40:245–256 (1983); Lepow, *Pediat. Infect. Dis. J.* 6:804–807 (1987), which references are incorporated herein by reference), and this model may be employed in constructing the vaccines of the present invention. Additional methods for producing a conjugate vaccine are disclosed by Anderson, et al., European Patent Publication 245,045; Anderson, et al, U.S. Pat. Nos. 4,673,574 and 4,761,283; Frank, et al., U.S. Pat. No. 4,789,735; European Patent Publication No. 206,852; Gordon, U.S. Pat. No. 4,619,828; and Beachey, U.S. Pat. No. 4,284,537, all of which references are incorporated herein by reference. Commonly used proteins that would be suitable include diptheria toxoid, tetanus toxoid, toxoids of exotoxin A, pseudomonas exotoxin and outer membrane bacterial proteins such as the outer membrane protein complex of Neisseria meningitidis.

Antibodies may also be generated in animals and then used in assays for detecting antigens indicative of enterococcal infection. The antibody selected for use should have at least a 100-fold greater affinity for one or more enterococcal strains than for any other type of bacterium. Methods for making and detecting such antibodies are well known to those of skill in the art, as evidenced by standard reference works such as: Harlow, et al, Antibodies, A Laboratory Manual, Cold Spring Harbor Laboratory, N.Y. (1988); Klein, Immunology: The Science of Self-Nonself Discrimination (1982); Kennett, et al., Monoclonal Antibodies and Hybridomas: A New Dimension in Biological Analyses (1980); and Campbell, "Monoclonal Antibody Technology," in Laboratory Techniques in Biochemistry and Molecular Biology (1984).

"Antibody," as used herein, is meant to include intact molecules as well as fragments which retain their ability to bind to antigen (e.g., Fab and F(ab')$_2$ fragments). These fragments are typically produced by proteolytically cleaving intact antibodies using enzymes such as papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al, Nature 256:495 (1975); Hammerling, et al, in Monoclonal Antibody and T-Cells Hybridomas, Elsevier, N.Y., pp. 563–681 (1981)). In general, this technology involves immunizing an animal, usually a mouse, with either intact polysaccharides or fragments derived from polysaccharides. The splenocytes of the immunized animals are extracted and fused with suitable myeloma cells, e.g., SPO cells. After fusion, the resulting hybridoma cells are selectively maintained in HAT medium and then cloned by limiting dilution (Wands, et al, Gastroenterology 80:225–232 (1981)). The cells obtained through such selection are then assayed to identify clones which secrete antibodies capable of binding to enterococcal strains.

The antibodies or fragments of antibodies of the present invention may be used to detect the presence of bacterial antigens in any of a variety of immunoassays. For example, antibodies may be used in radioimmunoassays or immunometric assays, also known as "two-site" or "sandwich" assays (see Chard, "An Introduction to Radioimmune Assays and Related Techniques," in Laboratory Techniques in Biochemistry and Molecular Biology, North Holland Publishing Co., N.Y. (1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see, e.g., Radioimmune Assay Method, Kirkham, et al., ed., pp. 199–206, E&S Livingstone, Edinburgh (1970)). Many variations of these types of assays are known in the art and may be employed for the detection of bacterial antigens.

Antibodies produced to polysaccharide antigens may also be used in purifications of the antigens (see generally Dean, et al., Affinity Chromatography, A Practical Approach, IRL Press (1986)). Typically, antibody is immobilized on a chromatographic matrix such as Sepharose 4B™ (Pharmacia. beaded agarose). The matrix is then packed into a column and the preparation containing antigen is passed through under conditions that promote binding (e.g, under conditions of low salt). The column is then washed and the bound antigen is eluted using a buffer that promotes dissociation from antibody, e.g., buffer having an altered pH or salt concentration. The eluted polysaccharide antigen may then be transferred into a buffer of choice, e.g., by dialysis, and either stored or used directly.

EXAMPLES

Example 1

Enterococcal capsular polysaccharide is purified from Enterococcal faecalis strain E1 (ATCC deposit number 202159) by growing the bacteria in dialyzed Columbia broth (cut-off MW 10,000) with the addition of hemin (0.0005%) and 5% glucose. The culture is oxygenated by bubbling $O_2$ through the growth medium at a rate of 2 liters per minute. After the culture ceases to use NaOH (i.e., after about 18 hours), cells are collected by centrifugation and then digested with mutanolysin/lysozyme (0.1 mg/ml, 37° C. for about 18 hours). The extract thus produced is treated with nucleases (DNase and RNase, 0.1 mg/ml each) at 37° C. for a period of about 8 hours and then digested with pronase E (0.1 mg/ml) at a temperature of 55° C. for a period of about 1 hours.

The preparation is next centrifuged and the resulting supernatant precipitated with four volumes of ethanol. The pellet is dissolved in distilled water or ammonium carbonate (0.4 M) and then size-fractionated on a Sephacryl S-500™ (Pharmacia Inc., cross-linked allyl dextran/N,N'-methylenebiscraylamide) column using ammonium carbonate buffer (0.4 M). The high molecular polysaccharides are found in the void volume and may be dialyzed and lyophilized. To remove contaminating cell wall antigens such as teichoic acids, two different strategies may be employed. Preparations may be treated with hydrogen fluoride (3 M at 4° C. for 24 hours) followed by neutralization with an equal amount of NaOH. Alternatively, preparations may be treated by ion exchange chromatography using a Q-column with Tris buffer (pH 7.3) and a NaCl gradient (0–1.0 M NaCl).

Evaluation of the resulting material for antigenicity is performed using an inhibition assay for opsonic killing activity. Inhibition of opsonic activity is achieved by adsorption of immune rabbit sera with 10–500 micrograms of purified polysaccharide for one hour at 4° C. This treatment should remove opsonic activity to levels comparable to normal rabbit sera in a dose-dependent manner. Alternatively, evaluations for antigenicity are performed using immunologic assays and antisera to the purified capsular polysaccharide that show that the purified material reacts with the specific antisera. Suitable radioimmunoassays and immunometric assays are described above.

Example 2

Rabbits were immunized with different gentamicin-killed Enterococcus faecalis strains and the sera of the rabbits were subsequently tested in an opsonophagocytic assay to quantify killing activity against both the homologous strain and a selection of 20 clinical isolates of Enterococci. Sera raised against one of the strains killed the homologous E. faecalis strain (E 1) at a dilution of 1:5120 and at a dilution of 1:500 effectively killed 5/15 (33%) of the additional clinical E. faecalis strains. In addition, sera raised against this strain killed 2/7 (28%) of a collection of vancomycin-resistant E.

faecium (VRE) strains, probably due to shared antigens between these two species.

Adsorption of the immune rabbit sera with the homologous strain removed the opsonic killing completely and the ability to adsorb out opsonic killing was resistant to treatment of bacteria with pronase E and to boiling for one hour. Treatment of the bacteria with sodium periodate (0.2 M, at room temperature for 24 hours) destroyed the cell's ability to adsorb out the opsonic killing activity, indicating a carbohydrate antigen as the likely target of the opsonic antibodies. Electron microscopic visualization of the bacterial cells using the immune rabbit sera in a negative staining reaction along with immunogold labeled anti-rabbit antibodies visualized a capsule-like structure in both the homologous strain and one of the VRE strains killed by the rabbit antibodies to *E. faecalis*. A high molecular weight fraction was isolated from strain E1 using digestion of bacterial cells with mutanolysin/lysozyme, treatment with nucleases and pronase E, and size fractionation on a Sephacryl S-300 column. The resulting material inhibited opsonic killing activity by the immune rabbit sera against both *E. faecalis* and *E. faecium* strains and, itself, elicited antibodies in rabbits. In summary, *E. faecalis* and *E. faecium* strains possess capsular polysaccharides which are targets of opsonophagocytic killing antibodies. These antigens may be used in the development of immunotherapeutic reagents for the treatment of enterococcal infections.

What is claimed is:

1. A method of generating antibodies that bind to *Enterococcus faecalis*, comprising administering a composition comprising the disaccharide:

6-α-D-GlcP-α-1→2[(2→1)-α-D-GlcP]-glycerol(PO$_4$)$_2$-3→ to a mammal at a dosage sufficient to induce the production of said antibodies.

2. A method of generating antibodies that bind to *Enterococcus faecalis* comprising administering an immunogenic polysaccharide to a mammal at a dosage sufficient to induce the production of said antibodies, wherein said immunogenic polysaccharide has the structure:

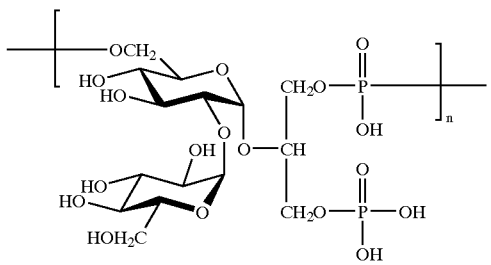

wherein n=2–5000.

3. The method of claim 2, wherein said immunogenic polysaccharide is unconjugated and n=200–5000.

4. The method of claim 2, wherein said immunogenic polysaccharide is conjugated to protein and n 2–2000.

5. The method of claim 2, wherein said immunogenic polysaccharide has been isolated by a process comprising the steps of:
   a) digesting an *E. faecalis* bacteria extract with nuclease and peptidase;
   b) size fractionating the digestion product of step a); and
   c) selecting those fractions containing said immunogenic polysaccharide.

6. The method of any one of claims 1 or 2–5, wherein said polysaccharide has been purified to remove teichoic acids.

7. A method of generating antibodies that bind to *Enterococcus faecalis*, comprising administering an immunogenic composition to a mammal, wherein:
   a) said composition comprises a substantially purified bacterial polysaccharide, wherein said bacterial polysaccharide comprises:
      i) repeating disaccharide units with the structure 6-α-D-GlcP-α-1→2[(2→1)-α-D-GlcP]-glycerol(PO$_4$)$_2$-3→, there being 2–5000 repetitions of said disaccharide unit in said bacterial polysaccharide;
      ii) a glycerol teichoic acid backbone linked to said disaccharide units via the number 2 carbon of glycerol;
      iii) phosphodiester bonds between the first carbon of the glycerol backbone and the sixth carbon of said disaccharide units;
   b) said composition is administered to said mammal at a dosage sufficient to induce the production of said antibodies.

* * * * *